United States Patent [19]

Wolf et al.

[11] Patent Number: 4,946,866
[45] Date of Patent: Aug. 7, 1990

[54] USE OF OXIRANCARBOXYLIC ACIDS FOR THE TREATMENT OF HYPERLIPEMIA

[75] Inventors: Horst Wolf, Allensbach; Klaus Eistetter, Constance, both of Fed. Rep. of Germany

[73] Assignee: Byk Gulden Lomberg Chemische Fabrik GmbH, Constance, Fed. Rep. of Germany

[21] Appl. No.: 44,499
[22] PCT Filed: Jul. 29, 1986
[86] PCT No.: PCT/EP86/00450
§ 371 Date: Mar. 27, 1987
§ 102(e) Date: Mar. 27, 1987
[87] PCT Pub. No.: WO87/00751
PCT Pub. Date: Feb. 12, 1987

[30] Foreign Application Priority Data

Aug. 2, 1985 [DE] Fed. Rep. of Germany ....... 3527800

[51] Int. Cl.$^5$ .......................................... A61K 31/335
[52] U.S. Cl. ..................................... 514/475; 514/824
[58] Field of Search ................ 562/405; 514/824, 449, 514/467, 475

[56] References Cited

U.S. PATENT DOCUMENTS

| | | | |
|---|---|---|---|
| 4,235,923 | 11/1980 | Durham | 514/475 |
| 4,324,796 | 4/1982 | Eistetter et al. | 514/475 |
| 4,337,267 | 6/1982 | Eistetter et al. | 514/475 |
| 4,430,339 | 2/1984 | Eistetter et al. | 514/475 |

FOREIGN PATENT DOCUMENTS 0046590 9/1982 European Pat. Off. ............ 514/467

OTHER PUBLICATIONS

*The Merck Manuel*, 14th Ed. (1982); pp. 386–389; 970–981; and 1037–1042.
Koundakjian et al., "Metabolic Changes in Fed Rats—Caused by Chronic Administration of Ethyl 2[5(4-chlorophenyl)pentyl]oxirane-2-carboxylate, A New Hypoglycemic Compound", Biochem. Pharmacology, vol. 33, No. 3, pp. 465–473, 1984.

*Primary Examiner*—Douglas W. Robinson
*Attorney, Agent, or Firm*—Berman, Aisenberg & Platt

[57] ABSTRACT

Use of oxirancarboxylic acids of formula I

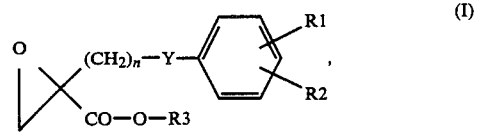

wherein
R1 is a hydrogen atom, a halogen atom, a 1–4C-alkyl group, a 1–4C-alkoxy group, a nitro group, or a trifluoromethyl group;
R2 has one of the meanings of R1;
R3 is a hydrogen atom or a 1–4C-alkyl group;
Y is the group —O—$(CH_2)_m$—;
m is 0 or a whole number from 1 to 4 and
n is a whole number between 2 and 8, for the prevention and/or treatment of illnesses which are associated with an increased cholesterol and/or triglyceride concentration.

17 Claims, No Drawings

USE OF OXIRANCARBOXYLIC ACIDS FOR THE TREATMENT OF HYPERLIPEMIA

This invention relates to the new use of known oxirancarboxylic acids for making lipid-lowering medications. The medications are used for the prevention and treatment of diseases which are based on an increased cholesterol and/or triglyceride concentration.

STATE OF THE ART

EP-A-0 046 590 describes hypoglycemically and hypoketonemically effective phen(alk)oxy-substituted oxirancarboxylic acids which are to be used for the treatment of diabetes. The magazine Biochemical Pharmacology, 33, 465 (1984) reports on the cholesterol and triglyceride concentration-lowering property of 2-[5-(4-chlorphenyl)-pentyl]-oxiran-2-carboxylic-acid-ethylesters.

DESCRIPTION OF INVENTION

It has now been found that the oxirancarboxylic acids, known from EP-A-0 046 590 bring about a definite lowering of the cholesterol and triglyceride concentration. Surprisingly, the extent of the reduction of the cholesterol and triglyceride concentration is considerably greater than one might have expected on the basis of the data collected for 2-[5-(4-chlorphenyl)-pentyl]-oxiran-2-carboxylic-acid-ethyl-esters. The surprisingly intensive reduction of the cholesterol and triglyceride concentration makes it appear that the oxirancarboxylic acids, which are known from EP-A-0 046 590, are suitable for use in the prevention and treatment of those diseases that are based on increased cholesterol and/or triglyceride concentration.

The object of the invention therefore is the use of oxirancarboxylic acids shown in Formula I

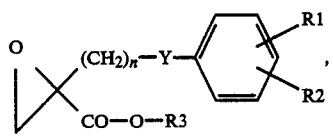

where
R1 is a hydrogen atom, a halogen atom a 1–4C-alkyl group, a 1–4C-alkoxy group, a nitro group, or a trifluoromethyl group;
R2 has one of the meanings of R1;
R3 is a hydrogen atom or a 1–4C-alkyl group;
Y is the group $-O-(CH_2)_m-$;
m is 0 or a whole number from 1 to 4 and
n is a whole number from 2 to 8,
whereby the sum of m and n is a whole number between 2 and 8 and the pharmacologically tolerable salts of carboxylic acids, for the production of medications for the prevention and/or treatment of diseases that are based on an increased cholesterol and/or triglyceride concentration.

As 1–4C-alkyl groups, one can consider straight-chain or ramified alkyl remnants with 1 to 4 carbon atoms. Straight-chain alkyl remnants, for example are the methyl-, ethyl-, n-propyl- and n-butyl remnants of which the methyl-and ethyl- remnant are preferred. Ramified alkyl remnants for example are isopropyl-, isobutyl-, secondary-butyl- and tertiary-butyl remnants. As alkyl remnants of 1–4C-alkoxy groups, one can consider both straight-chain and ramified low-alkyl groups. The methoxy group is preferred as 1–4C-alkoxy group.

Halogen atoms are fluorine, chlorine, and bromine atoms of which fluorine and especially chlorine are preferred.

The substituents R1 and R2 of the phenyl ring are preferably in the meta- or para-positions with respect to the (alk)oxyalkylene-oxirancarboxylic acid remnant.

As salts one can consider salts with inorganic and organic bases. As cations for salt formation one uses above all the cations of the alkali metals, earth-alkali metals, or earth metals. By way of example we might mention the salts of lithium, sodium, potassium, magnesium, calcium, and aluminum.

As diseases, which are based on an increased cholesterol and/or triglyceride concentration (hyperlipemia), we might mention primarily all forms of arteriosclerosis, especially coronary sclerosis and all of the pathological changes connected with this, which can be combined under the collective term of "coronary heart disease."

If the compounds in Formula I are used according to the invention for the manufacture of the above-mentioned medications, then the compounds of Formula I (=active substances) are employed either as such or preferably in combination with suitable pharmaceutical auxiliary or carrier substances in the form of tablets, coated tablets, capsules, suppositories, emulsions, suspensions, or solutions, where the active-substance content advantageously is between 0.1 and 95%.

The expert in the field knows, on the basis of his technical knowledge, which auxiliary or carrier substances are suitable for the desirable medication formulations. In addition to solvents, gel-forming agents, suppository foundations, auxiliary tablet substances and other active-substance carriers, one might for example use antioxidants, dispersion agents, emulsifiers, despumators, taste correction agents, conservation agents, solution mediators, dyes or special permeation promoters and complex-forming agents (for example, cyclodextrins).

The active substances can be administered orally or parenterally.

In general, it proved advantageous in human medicine to administer the active substance or substances, in case of oral administration, in a daily dose of about 0.1 to about 30, preferably 0.3 to 15, especially 0.6 to 3 mg/kg of body weight, possibly in the form of several, preferably 1 to 4 individual administrations, for the treatment of the desired results. In case of parenteral treatment, one cae use similar dosages or (especially in case of intravenous administration of active substances) as a rule lower dosages. The determination of the particular necessary optimum dosage and manner of application of active substances can usually be made by any expert on the basis of his technical knowledge.

If the active substances are to be used for the treatment of the above-mentioned diseases, then the medications, obtained as a result of the use of the active substances according to the invention, can also contain one or more other pharmacologically active compounds, especially other so-called lipid-lowering substances, such as p-aminosalicycli acid, D-thyroxin, nicotinic acid, sitosterols, cholestyramin, clofibrate, ciprofibrate, probucol, cholestipol, gemfibrozil, fenofibrate, or bezafibrate.

Another object of the invention is the use of compounds of Formula I in the prevention and/or treatment of diseases based on an increased cholesterol and/or triglyceride concentration.

An embodiment of the invention is the use of oxirancarboxylic acids of Formula I, wherein R1 and R2 are in meta- or para-position and where R1 is a hydrogen atom, a chlorine atom, a methyl group, a methoxy group, a nitro group, or a trifluoromethyl group, R2 is a hydrogen atom or a chlorine atom, R3 is a hydrogen atom or a 1–4C-alkyl group, Y is the grouping —O—$(CH_2)_m$—, m is 0 or 1, and n is a whole number between 3 and 7, whereby the sum of m and n is a whole number between 3 and 7, and the pharmacological tolerable salts of carboxylic acids, for the production of medications for the prevention and/or treatment of diseases based on an increased cholesterol and/or triglyceride concentration.

A further embodiment of the invention is the use of oxirancarboxylic acids of Formula I where R1 is in meta- or para-position and where R1 is a hydrogen atom, a chlorine atom, or a trifluoromethyl group, R2 is a hydrogen atom, R3 is a hydrogen atom, a methyl group or an ethyl group, Y is the grouping —O—, n is a whole number between 4 and 6, and the pharmacologically tolerable salts of carboxylic acids for the production of medications for the prevention and/or treatment of diseases which are based on an increased cholesterol and/or triglyceride concentration.

A preferred embodiment of the invention is the use of one or more oxirancarboxylic acids selected from among a group consisting of 2-[4-(3-chlorophenoxy)-butyl]-oxiran-2-carboxylic acid-ethyl-ester, 2-[4-3-trifluoromethylphenoxy)-butyl]-oxiran-2-carboxylic acid-ethyl ester, 2-[6-(4-chlorophenoxy)-hexyl]-oxiran-2-carboxylic acid-ethyl-ester, 2-[5-(4-chlorophenoxy)-pentyl]-oxiran-2-carboxylic-acid-ethyl-ester, 2-[6-(3,4-dichlorophenoxy)-hexyl]-oxiran-2-carboxylic acid-ethyl-ester, 2-[6-(4-fluorophenoxy)-hexyl]-oxiran-2-carboxylic-acid-ethyl-ester and 2-[6-phenoxyhexyl]-oxiran-2-carboxylic-acid-ethyl-ester as well as the corresponding oxiran-2-carboxylic acids and their pharmacologically tolerable salts, for the production of medications for the prevention and/or treatment of diseases based on an increased cholesterol and/or triglyceride concentration.

A particularly preferred embodiment of the invention is the use of 2-[6-(4-chlorophenoxy)hexyl]-oxiran-2-carboxylic acid-ethyl-ester for the production of medications for the prevention and/or treatment of diseases based on an increased cholesterol and/or triglyceride concentration.

EXAMPLE OF PHARMACEUTICAL FORMULATION

Soft gelatin capsules with a content of 100 mg 525 g 2-[6-(4-chlorophenoxy)hexyl]-oxiran-2-carboxylic-acid-ethyl-ester are carefully mixed with 1,764 g of a mixture made up of emulsifier (for example, Cremophor ® RH40) and neutral oil (for example, Miglyol 812) in a ratio of, for example, 1:16 to 16:1. In each case, 436 mg of the mixture are poured into size 8 soft gelatin capsules.

PHARMACOLOGY

In terms of their cholesterol and triglyceride concentration-lowering properties, within the context of an animal experiment, the compounds of Formula I (especially 2-[6-(4-chlorophenoxy)hexyl]-oxiran-2-carboxylic-acid-ethyl-ester=compound B) proved to be clearly, and quite surprisingly superior to 2-[5-(4-chorophenyl)pentyl]-oxiran-2-carboxylic-acid-ethyl-ester=compound A. This superiority emerges from a comparison of the cholesterol reduction in the serum of sober rats (Table 1) which was determined as a function of the time following a single oral administration of 0.05 mol/kg of the compounds.

| Compound | % Change in Plasmacholesterol compared to control group (n = 12) | | |
| --- | --- | --- | --- |
| | 2-3 | 4-5 | 24 hp. appl. |
| A | +14 | +12 | −30 |
| B | +6 | −16 | −46 |

The pharmacological data were determined according to the following methods.

1. Dosage

Onetime administration of 0.05 mmol/kg of Compound A in an aqueous solution or B in an aqueous emulsion with the addition of 2 parts by weight of Cremophor ®-EL (BASF, Ludwigshafen). The application volume was 10 ml/kg and it was administered by means of stomach probe.

2. Experimental Animals

Male SD rats of the SPF breed Ivanovas (Kisslegg), with a body weight of 255–440 g were used as experimental animals. The animals were kept in a conventional manner with 4 animals, each, in Makrolon cages (22×38 cm) in a temperature-controlled room (21°–23° C.) with a fixed day/night rhythm (0700/1900) and regulated relative air humidity of 55–60%. Until 24 hours prior to the start of the experiment, the animals were given a maintenance diet of Altromin 1324 made by the Firm of Altromin (Lage). The animals were given as much water as they wanted [ad libitum].

3. Methodology

The animals were subdivided at random in groups of 12 animals, each. The control group received water instead of the substance solution. The experiment was started in the morning with the taking of blood for preliminary value determination. The substance was administered immediately thereafter and additional blood samples were taken in a retro-orbital manner for cholesterol determination at the times indicated in Table 1.

4. Determination Method

The cholesterol was determined in the plasma which had been obtained by means of centrifugation of the heparinized blood samples in accordance with the CHOD-PAP method according to Trinder, P., Ann. Clin. Biochem., 6, 24 (1969) by means of the test combination supplied by the Firm of Boehringer/Mannheim, Order No. 187 313.

5. Analysis

The analysis was performed by means of a computer program ("Screeny") which-after elimination of extreme values according to the method of Dixon, W. J., Biometrics 9, 74 (1953)—computed mean values, standard deviations, and percentage changes compared to the control group. The latter are given in Table 1.

We claim:

1. A method of reducing cholesterol and/or triglyceride concentrations in a subject in need thereof comprising administering to the subject a therapeutically effective amount of an oxirancarboxylic acid of Formula I

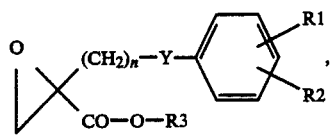

wherein
- R1 is a hydrogen atom, a halogen atom, a 1-4C-alkyl group, a 1-4C-alkoxy group, nitro or trifluoromethyl;
- R2 has one of the meanings of R1;
- R3 is a hydrogen atom;
- Y is —O—(CH$_2$)$_m$—;
- m is zero or a whole number between 1 and 4;
- n is a whole number between 2 and 8, and
- m+n is a whole number between 2 and 8;
- a pharmacologically-acceptable salt of the carboxylic acid, or an ester of the carboxylic acid wherein R3 is a 1-4C-alkyl group.

2. A method of claim 1 to a host subject to or afflicted with such disease;
wherein
- R1 is a hydrogen atom, chloro, methyl, methoxy, nitro or trifluoromethyl;
- R2 is a hydrogen atom or chloro;
- each of R1 and R2 is in meta or para position;
- m is zero or 1;
- n is a whole number between 3 and 7; and
- m+n is a whole number between 3 and 7, or
- a pharmacologically-acceptable salt of the oxirancarboxylic acid.

3. A method of claim 1
wherein
- R1 is a hydrogen atom, chloro or trifluoromethyl;
- R2 is a hydrogen atom;
- each of R1 and R2 is in meta or para position;
- R3 is a hydrogen atom, methyl or ethyl;
- Y is —O—; and
- n is a whole number between 4 and 6, or
- a pharmacologically-acceptable salt of the oxirancarboxylic acid.

4. A method of claim 1 wherein the oxirancarboxylic acid is a member selected from the group consisting of 2-[4-(3-chlorophenoxy)-butyl]-oxiran-2-carboxylic acid-ethyl-ester, 2-[4-(3-trifluoromethylphenoxy)-butyl]-oxiran-2-carboxylic acid-ethyl-ester, 2-[6-(4-chlorophenoxy)-hexyl]-oxiran-2-carboxylic acid-ethyl-ester, 2-[5-(4-chlorophenoxy)-pentyl]-oxiran-2-carboxylic acid-ethyl-ester, 2-[6-(3,4-dichlorophenoxy)-hexyl]-oxiran-2carboxylic acid-ethyl-ester, 2-[6-(4-fluorophenoxy)-hexyl]-oxiran-2-carboxylic acid-ethyl-ester, 2-(6-phenoxyhexyl)-oxiran-2-carboxylic acid-ethyl-ester, the carboxylic acid corresponding to each ester and a pharmacologically-acceptable salt of each such acid.

5. A method of claim 1 wherein the oxirancarboxylic acid is 2-[6-(4-chlorophenoxy)hexyl]-oxiran-2-carboxylic acid-ethyl-ester.

6. A method of claim 1 wherein m is a whole number from 1 to 4, inclusive.

7. A method of claim 3 wherein R1 is a hydrogen atom.

8. A method of claim 7 wherein n is 5.

9. A method of claim 7 wherein n is 6.

10. A method of claim 1 wherein
- R1 is a halogen atom;
- R2 is a hydrogen atom;
- R3 is a hydrogen atom, methyl or ethyl;
- Y is —O—; and
- n is a whole number between 4 and 6.

11. A method of claim 10 wherein n is 5.

12. A method of claim 10 wherein n is 6.

13. A method which comprises administering to a human or other animal subject, subject to or afflicted with a disease based on an increased cholesterol concentration, an increased triglyceride concentration or an increased cholesterol and triglyceride concentration, an amount of active ingredient effective to reduce at least one of (a) the cholesterol concentration, (b) the triglyceride concentration and (c) the cholesterol and the triglyceride concentration in the subject, and wherein the active ingredient comprises an oxirancarboxylic acid of Formula I

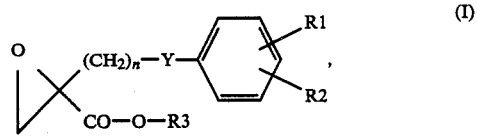

wherein
- R1 is a hydrogen atom, a halogen atom, a 1-4C-alkyl group, A 1-4C-alkoxy group, nitro or trifluoromethyl;
- R2 has one of the meanings of R1;
- R3 is a hydrogen atom;
- Y is —O—(CH$_2$)$_m$;
- m is zero or a whole number between 1 and 4;
- n is whole number between 2 and 8; and
- m+n is a whole number between 2 and 8; a pharmacologically-acceptable salt of the carboxylic acid, or an ester of the carboxylic acid wherein R3 is a 1-4C-alkyl group.

14. A method according to claim 13 wherein the disease is hyperlipemia.

15. A method according to claim 13 wherein the disease is arteriosclerosis.

16. A method according to claim 13 wherein the disease is coronary sclerosis.

17. A method according to claim 13 wherein the disease is coronary heart disease.

* * * * *